(12) United States Patent
Fittschen et al.

(10) Patent No.: US 6,849,646 B1
(45) Date of Patent: Feb. 1, 2005

(54) CHROMENONE AND CHROMANONE DERIVATIVES AS INTEGRIN INHIBITORS

(75) Inventors: Claus Fittschen, Fränkisch-Crumbach (DE); Simon Goodman, Darmstadt (DE); Joachim März, Gross-Gerau (DE); Peter Raddatz, Alsbach (DE); Matthias Wiesner, Mainz (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/830,285

(22) PCT Filed: Oct. 14, 1999

(86) PCT No.: PCT/EP99/07725

§ 371 (c)(1),
(2), (4) Date: Apr. 25, 2001

(87) PCT Pub. No.: WO00/26212

PCT Pub. Date: May 11, 2000

(30) Foreign Application Priority Data

Oct. 31, 1998 (DE) .......................... 198 50 131

(51) Int. Cl.$^7$ ...................... A61K 31/44; A61K 31/415; A61K 31/35; C07D 233/66; C07D 421/00
(52) U.S. Cl. ...................... 514/336; 514/385; 514/456; 548/331.5; 546/268.1; 549/406
(58) Field of Search ................. 514/397, 385, 514/336, 456; 548/311.4, 331.5; 546/268.1; 549/406

(56) References Cited

U.S. PATENT DOCUMENTS 5,703,075 A  12/1997  Gammill ................. 514/233.5

FOREIGN PATENT DOCUMENTS

| EP | 341 104 | 11/1989 |
|----|---------|---------|
| WO | 90 06921 | 6/1990 |
| WO | 91 19707 | 12/1991 |
| WO | 96 22288 | 7/1996 |

*Primary Examiner*—Alan L. Rotman
*Assistant Examiner*—Binta Robinson
(74) *Attorney, Agent, or Firm*—Millen, White, Zelano & Branigan, P.C.

(57) ABSTRACT

The invention relates to compounds having formula (I), wherein $R^1$, $R^2$, $R^3$, $R^4$, $R^5$, $R^7$, $R^8$, $R^{11}$, Z, m and n have the meaning cited in claim 1, and to the physiologically acceptable salts and solvates which can be used as integrin inhibitors, especially in the prophylaxis and treatment of circulatory diseases, in case of thrombosis, myocardial infarction, coronary heart diseases, arteriosclerosis, osteoporosis, pathologic processes caused or propagated by angiogenesis and in tumor therapy.

24 Claims, No Drawings

CHROMENONE AND CHROMANONE DERIVATIVES AS INTEGRIN INHIBITORS

This application is a 371 PCT/EP99/07725 filed Oct. 14, 1999.

The invention relates to compounds of the formula I

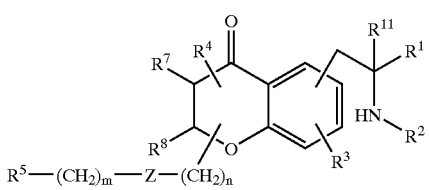

in which
- $R^1$ is $CH_2OR^{10}$, $COOR^{10}$, $CONHR^{10}$ or $CON(R^{12})_2$,
- $R^2$ is $R^{10}$, $CO-R^{10}$, $CO-R^6$, $COOR^{10}$, $COOR^{10}$, $SO_2R^6SO_2R^{10}$, $CONHR^6$, $CON(R^6)_2$, $CONHR^{10}$ or $CON(R^{12})_2$,
- $R^3$ is H, Hal, $NHR^{10}$, $N(R^{12})_2$, —NH-acyl, —O-acyl, CN, $NO_2$, $OR^{10}$, $SR^{10}$, $SO_2R^{10}$, $SO_3R^{10}$, $COOR^{10}$, $CONHR^6$, $CON(R^6)_2$, $CONHR^{10}$ or $CON(R^{12})_2$,
- $R^4$ is H, A, Ar or aralkylene having 7–14 C atoms,
- $R^5$ is $NH_2$, $H_2N-C(=NH)$ or $H_2N-(C=NH)-NH$, where the primary amino groups can also be provided with conventional amino protective groups, or can be mono- di- or trisubstituted by $R^{10}$, $CO-R^{10}$, $COOR^{10}$ or $SO_2R^{10}$, or is $R^6-NH-$,
- $R^6$ is a mono- or binuclear heterocycle having 1 to 4 N, O and/or S atoms, which can be unsubstituted or mono-, di- or trisubstituted by Hal, A, —CO-A, OH, CN, COOH, COOA, $CONH_2$, $NO_2$, =NH or =O,
- $R^7$, $R^8$ in each case independently of one another is absent or is H,
- $R^7$ and $R^8$ together are also a bond,
- Z is absent, O, S, NH, $NR^1$, C(=O), CONH, NHCO, C(=S)NH, NHC(=S), C(=S), $SO_2NH$, $NHSO_2$ or CA=CA',
- $R^9$ is H, Hal, $OR^{11}$, $NH_2$, $NHR^{12}$, $N(R^{12})_2$, NHAcyl, OAcyl, CN, $NO_2$, $SR^{11}$, $SOR^{12}$, $SO_2R^{12}$ or $SO_3H$,
- $R^{10}$ is H, A, Ar or aralkylene having 7–14 C atoms,
- $R^{11}$ is H or alkyl with 1–6 C atoms,
- $R^{12}$ is alkyl having 1–6 C atoms,
- A is H or alkyl having 1–15 C atoms or cycloalkyl having 3–15 C atoms, which is unsubstituted or is mono-, di- or trisubstituted by $R^9$ and in which one, two or three methylene groups can also be replaced by N, O and/or S,
- Ar is a mono- or binuclear aromatic ring system having 0, 1, 2, 3 or 4 N, O and/or S atoms, which is unsubstituted or mono-, di- or trisubstituted by A and/or $R^9$,
- Hal is F, Cl, Br or I and
- m, n in each case independently of one another are 0, 1, 2, 3 or 4, and their physiologically acceptable salts and solvates.

Similar compounds are disclosed, for example, in WO 94/29273, WO 96/00730 and WO 96/18602.

The invention is based on the object of finding novel compounds having useful properties, in particular those which can be used for the production of medicaments.

It has been found that the compounds of the formula I and their salts and solvates have very useful pharmacological properties, together with good tolerability. Above all, they act as integrin inhibitors, inhibiting, in particular, the interactions of the $\alpha_v$ integrin receptors with ligands. The compounds show particular activity in the case of the integrins $\alpha_v\beta_3$ and $\alpha_v\beta_5$. The compounds are very particularly active as adhesion receptor antagonists for the vitronectin receptor $\alpha_v\beta_3$.

This action can be demonstrated, for example, according to the method which is described by J. W. Smith et al., in J. Biol. Chem. 265, 11008–11013 and 12267–12271 (1990).

In Curr. Opin. Cell. Biol. 5, 864 (1993), B. Felding-Habermann and D. A. Cheresh describe the importance of the integrins as adhesion receptors for all sorts of phenomena and syndromes, especially in relation to the vitronectin receptor $\alpha_v\beta_3$.

The dependence of the origin of angiogenesis on the interaction between vascular integrins and extracellular matrix proteins is described by P. C. Brooks, R. A. Clark and D. A. Cheresh in Science 264, 569–71 (1994).

The possibility of the inhibition of this interaction and thus of initiating apoptosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157–64 (1994).

The experimental proof that the compounds according to the invention also prevent the adhesion of living cells to the corresponding matrix proteins and accordingly also prevent the adhesion of tumour cells to matrix proteins can be furnished in a cell adhesion test which is carried out analogously to the method of F. Mitjans et al., J. Cell Science 108, 2825–2838 (1995).

In J. Clin. Invest. 96, 1815–1822 (1995), P. C. Brooks et al. describe $\alpha_v\beta_3$ antagonists for the control of cancer and for the treatment of tumour-induced angiogenic diseases.

The compounds of the formula I according to the invention can therefore be employed as pharmaceutical active compounds, in particular for the treatment of oncoses, osteoporoses, osteolytic disorders and for the suppression of angiogenesis.

Compounds of the formula I which block the interaction of integrin receptors and ligands, such as, for example, of fibrinogen to the fibrinogen receptor (glycoprotein IIb/IIIa), prevent, as GPIIb/IIIa antagonists, the spread of tumour cells by metastasis. This is confirmed by the following observations:

The spread of tumour cells from a local tumour into the vascular system takes place through the formation of microaggregates (microthrombi) by interaction of the tumour cells with blood platelets. The tumour cells are screened by the protection in the microaggregate and are not recognized by the cells of the immune system.

The microaggregates can collect on vascular walls, whereby a further penetration of tumour cells into the tissue is facilitated. Since the formation of the microthrombi is mediated by fibrinogen binding to the fibrinogen receptors on activated blood platelets, the GPIIa/IIIb antagonists can be regarded as efficacious metastasis inhibitors.

In addition to the binding of fibrinogen, fibronectin and of the [lacuna] Willebrand factor to the fibrinogen receptor of the blood platelets, compounds of the formula I also inhibit the binding of other adhesive proteins, such as vitronectin, collagen and laminin, to the corresponding receptors on the surface of various cell types. They prevent, in particular, the formation of blood platelet thrombi and can therefore be employed for the treatment of thromboses, apoplexy, cardiac infarct, inflammations and arteriosclerosis.

The properties of the compounds can also be demonstrated by methods which are described in EP-A1-0 462 960. The inhibition of fibrinogen binding to the fibrinogen receptor can be detected by the method which is given in EP-A1-0 381 033.

The platelets aggregation-inhibiting action can be demonstrated in vitro by the method of Born (Nature 4832, 927–929, 1962).

The invention accordingly relates to the compounds of the formula I according to claim 1 and their physiologically acceptable salts and solvates as GPIIb/IIIa antagonists for the control of thromboses, cardiac infarcts, coronary heart disorders and arteriosclerosis.

The invention furthermore relates to the compounds of the formula I according to claim 1 and their physiologically acceptable salts and solvates for the production of a medicament for use as integrin inhibitors.

The invention relates in particular to compounds of the formula I according to claim 1 and their acceptable salts and solvates for the production of a medicament for the control of pathological angiogenic disorders, tumours, osteoporosis, inflammations and infections.

The compounds of the formula I can be employed as pharmaceutical active compounds in human and veterinary medicine, for the prophylaxis and/or therapy of thrombosis, myocardial infarct, arteriosclerosis, inflammations, apoplexy, angina pectoris, oncoses, osteolytic diseases such as osteoporosis, pathological angiogenic diseases such as, for example, inflammations, ophthalmological diseases, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, restenosis after angioplasty, viral infection, bacterial infection, fungal infection, in acute kidney failure and in wound healing for assisting the healing processes.

The compounds of the formula I can be employed as antimicrobial substances in operations where biomaterials, implants, catheters or heart pacemakers are used. They have an antiseptic action here. The efficacy of the antimicrobial activity can be demonstrated by the process described by P. Valentin-Weigund et al., in Infection and Immunity, 2851–2855 (1988).

The invention furthermore relates to a process for the preparation of compounds of the formula I according to claim 1 and of their salts and solvates, characterized in that
a) a compound of the formula I is liberated from one of its functional derivatives by treating with a solvolysing or hydrogenolysing agent, or
b) a radical $R^1$, $R^2$ and/or $R^5$ is converted into another radical $R^1$, $R^2$ and/or $R^5$ by, for example,
   i) converting an amino group into a guanidino group by reaction with an amidinating agent,
   ii) hydrolysing an ester,
   iii) reducing a carboxylic acid to an alcohol,
   iv) converting a hydroxyamidine into an amidine by hydrogenation
and/or converting a base or acid of the formula I into one of its salts.

The compounds of the formula I have at least one chiral centre and can therefore occur in a number of stereoisomeric forms. All these forms (e.g. D and L forms) and their mixtures (e.g. the DL forms) are included in the formula I.

So-called prodrug derivatives are also included in the compounds according to the invention, i.e. compounds of the formula I modified with, for example, alkyl or acyl groups, sugars or oligopeptides, which are rapidly cleaved in the body to give the active compounds according to the invention.

Solvates of the compounds are also included in the compounds according to the invention. Amongst these are understood addition compounds with, for, example, water (hydrates) or alcohols such as methanol or ethanol.

The abbreviations mentioned above and below stand for:

| | |
|---|---|
| Ac | Acetyl |
| BOC | tert-Butoxycarbonyl |
| CBZ or Z | Benzyloxycarbonyl |
| DCCI | Dicyclohexylcarbodiimide |
| DMF | Dimethylformamide |
| DOPA | (3,4-Dihydroxyphenyl)alanine |
| DPFN | 3,5-Dimethylpyrazole-1-formamidinium nitrate |
| DMAP | Dimethylaminopyridine |
| EDCI | N-Ethyl-N,N'-(dimethylaminopropyl)carbodiimide |
| Et | Ethyl |
| Fmoc | 9-Fluorenylmethoxycarbonyl |
| HOBt | 1-Hydroxybenzotriazole |
| Me | Methyl |
| MTB ether | Methyl tert-butyl ether |
| Mtr | 4-Methoxy-2,3,6-trimethylphenylsulfonyl |
| HONSu | N-Hydroxysuccinimide |
| Np | Neopentyl |
| OBn | Benzyl ester |
| OBut | tert-Butyl ester |
| Oct | Octanoyl |
| OMe | Methyl ester |
| OEt | Ethyl ester |
| Orn | Ornithine |
| POA | Phenoxyacetyl |
| TBTU | O-(Benzotriazol-1-yl)-N,N,N,N-tetramethyluronium tetrafluoroborate |
| TFA | Trifluoroacetic acid |
| pTSS salt | para-Toluenesulfonic acid salt |
| Trt | Trityl (triphenylmethyl) |
| Z or CBZ | Benzyloxycarbonyl. |

It applies to the whole invention that all radicals which occur a number of times can be identical or different, i.e. are independent of one another.

In the above formulae, alkyl is preferably methyl, ethyl, propyl, isopropyl, butyl, isobutyl, sec-butyl or tert-butyl, in addition also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2-, 1,2,2-trimethylpropyl, heptyl, octyl, nonyl or decyl.

Cycloalkyl is preferably cyclopropyl, cyclobutyl, cyclopentyl, cyclohexyl, cycloheptyl, adamantyl or 3-menthyl. Cycloalkyl is in particular the radical of a bicyclic terpene; the camphor-10-yl radical is very particularly preferred:

Alkylene is preferably methylene, ethylene, propylene, butylene, pentylene, in addition also hexylene, heptylene, octylene, nonylene or decylene. Aralkylene is preferably alkylenephenyl and is, for example, preferably benzyl or phenethyl.

Cycloalkylene is preferably cyclopropylene, 1,2- or 1,3-cyclobutylene, 1,2- or 1,3-cyclopentylene, 1,2-, 1,3- or 1,4-cyclohexylene, in addition also 1,2-, 1,3- or 1,4'-cycloheptylene.

CO-A is alkanoyl or cycloalkanoyl and is preferably formyl, acetyl, propionyl, butyryl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl or octadecanoyl.

Acyl is $C_1$–$C_7$-acyl and has 1, 2, 3, 4, 5, 6 or 7 C atoms and is preferably, for example, formyl, acetyl, propionyl, butyryl, trifluoroacetyl or benzoyl.

Preferred substituents $R^9$ for alkyl, alkylene, cycloalkyl, cycloalkylene, alkanoyl, cycloalkanoyl and aryl are, for example, Hal, $OR^{11}$, $NHR^{12}$, $N(R^{12})_2$, CN, $NO_2$, $SR^{11}$, $SOR^{12}$, $SO_2R^{12}$ and/or $SO_3H$, in particular, for example, F, Cl, hydroxyl, methoxy, ethoxy, amino, dimethylamino, methylthio, methylsulfinyl, methylsulfonyl or phenylsulfonyl.

In the radicals alkyl, alkylene, cycloalkyl, cycloalkylene, alkanoyl and cycloalkanoyl, one, two or three methylene groups in each case can be replaced by N, O and/or S.

Ar—CO is aroyl and is preferably benzoyl or naphthoyl.

Ar is unsubstituted, preferably—as indicated—monosubstituted phenyl, specifically preferably phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-cyanophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-methylthiophenyl, o-, m- or p-methylsulfinylphenyl, o-, m- or p-methylsulfonylphenyl, o-, m- or p-aminophenyl, o-, m- or p-methylaminophenyl, 0-, m- or p-dimethylaminophenyl, o-, m- or p-nitrophenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2-chloro-3-methyl-, 2-chloro-4-methyl-, 2-chloro-5-methyl-, 2-chloro-6-methyl-, 2-methyl-3-chloro-, 2-methyl-4-chloro-, 2-methyl-5-chloro-, 2-methyl-6-chloro-, 3-chloro-4-methyl-, 3-chloro-5-methyl- or 0.3-methyl-4-chlorophenyl, 2-bromo-3-methyl-, 2-bromo-4-methyl-, 2-bromo-5-methyl-, 2-bromo-6-methyl-, 2-methyl-3-bromo-, 2-methyl-4-bromo-, 2-methyl-5-bromo-, 2-methyl-6-bromo-, 3-bromo-4-methyl-, 3-bromo-5-methyl- or 3-methyl-4-bromophenyl, 2,4- or 2,5-dinitrophenyl, 2,5- or 3,4-dimethoxyphenyl, 2,3,4-, 2,3,5-, 2,3,6-, 2,4,6- or 3,4,5-trichlorophenyl, 2,4,6-tri-tert-butylphenyl, 2,5-dimethylphenyl, p-iodophenyl, 4-fluoro-3-chlorophenyl, 4-fluoro-3,5-dimethylphenyl, 2-fluoro-4-bromophenyl, 2,5-difluoro-4-bromophenyl, 2,4-dichloro-5-methylphenyl, 3-bromo-6-methoxyphenyl, 3-chloro-6-methoxyphenyl, 2-methoxy-5-methylphenyl, 2,4,6-triisopropylphenyl, naphthyl, 1,3-benzodioxol-5-yl, 1,4-benzodioxan-6-yl, benzothiadiazol-5-yl or benzoxadiazol-5-yl.

Furthermore, Ar is preferably 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadizol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, - 2-, 4-, 5-, 6- or 7-benzoxazolyl, 3-, 4-, 5-, 6- or 7-benziisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl.

Arylene has the same meanings as given for Ar, with the proviso that a further bond is linked from the aromatic system to the next adjacent bond.

Heterocycloalkylene is preferably 1,2-, 2,3- or 1,3-pyrrolidinyl, 1,2-, 2,4-, 4,5- or -1,5-imidazolidinyl, 1,2-, 2,3-, or 1,3-pyrazolidinyl, 2,3-, 3,4-, 4,5- or 2,5-oxazolidinyl, 1,2-, 2,3-, 3,4- or 1,4-isoxazolidinyl, 2,3-, 3,4-, 4,5- or 2,5-thiazolidinyl, 2,3-, 3,4-, 4,5- or 2,5-isothiazolidinyl, 1,2-, 2,3-, 3,4- or 1,4-piperidinyl, 1,4- or 1,2-piperazinyl, furthermore preferably 1,2,3-tetrahydrotriazol-1,2- or -1,4-yl, 1,2,4-tetrahydrotriazol-1,2- or 3,5-yl, 1,2- or 2,5-tetrahydrotetrazolyl, 1,2,3-tetrahydrooxadiazol-2,3-, -3,4-, -4,5- or -1,5-yl, 1,2,4-tetrahydro-oxadiazol-2,3-, -3,4- or -4,5-yl, 1,3,4-tetrahydro-thiadiazol-2,3-, -3,4-, -4,5- or -1,5-yl, 1,2,4-tetrahydrothiadiazol-2,3-, -3,4-, 4,5- or -1,5-yl, 1,2,3-thiadiazol-2,3-, -3,4-, -4,5- or -1,5-yl, 2,3- or 3,4-morpholinyl, 2,3-, 3,4- or 2,4-thiomorpholinyl.

$R^6$ is a mono- or binuclear heterocycle, preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5-, 6-, or 7-benzofuryl, 2-, 3-, 4-, 5-, 6- or 7-benzothienyl, 1-, 2-, 3-, 4-, 0.5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 0.6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 0.5-, 6-, 7- or 8-cinnolinyl, 2-, 4-, 5-, 6-, 7- or 8-quinazolinyl.

The heterocyclic radicals can also be partly or completely hydrogenated.

$R^6$ can thus, for example, also be 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4-, or -5-pyrrolyl, 2,5-dihydro-1-, -2-, -3-, -4-, or 5-pyrrolyl, 1-, 2- or 3-pyrrolidinyl, tetrahydro-1-, -2- or -4-imidazolyl, 2,3-dihydro-1-, -2-, -3-, -4-, or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, - 3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

The heterocyclic rings mentioned can also be mono-, di- or trisubstituted by Hal, A, —CO-A, OH, CN, COOH, COOA, $CONH_2$, $NO_2$, =NH or =O.

$R^5$ is very particularly preferably 1H-imidazol-2-yl, thiazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyridin-2-yl, pyrimidin-2-yl or 1,4,5,6-tetrahydropyrimidin-2-yl.

$R^1$ is in particular, for example hydroxymethyl, carboxyl, methoxycarbonyl, ethoxycarbonyl, $CONH_2$, CONHMe, $CONHEt$, $CONMe_2$ or $CONEt_2$.

$R^1$ is very particularly preferably carboxyl or ethoxycarbonyl.

$R^2$ is in particular, for example, methoxycarbonyl, ethoxycarbonyl, propoxycarbonyl, tert-butyloxycarbonyl, isobutyloxycarbonyl, 2,2-dimethylpropoxycarbonyl, methylsulfonyl, ethylsulfonyl, propylsulfonyl, butylsulfonyl, isobutylsulfonyl, 2,2-dimethylpropylsulfonyl, phenylsulfonyl or benzylsulfonyl.

$R^2$ is very particularly preferably 2,2-dimethylpropoxycarbonyl, 2,2-dimethylpropylsulfonyl, butylsulfonyl, phenylsulfonyl or benzylsulfonyl.

$R^3$ is preferably, for example, H, F, Cl, Br, amino, methylamino, ethylamino, dimethylamino, diethylamino, acetamido, acetoxy, cyano, nitro, methoxy, ethoxy, methylsulfonyl, phenylsulfonyl, p-tolylsulfonyl, carboxyl, methoxycarbonyl, ethoxycarbonyl, $CONH_2$, CONHMe or $CONMe_2$. $R^3$ is very particularly preferably H.

$R^4$ is preferably, for example, H, methyl, ethyl, propyl, isopropyl or butyl. $R^4$ is very particularly 10 preferably H.

$R^9$ is preferably, for example, H, F, Cl, Br, methoxy, ethoxy, propoxy, amino, methylamino, dimethylamino, ethylamino, diethylamino, acetamido, acetoxy, cyano, nitro, methylsulfonyl, phenylsulfonyl, p-tolylsulfonyl or $SO_3H$. $R^9$ is very particularly preferably H.

$R^{11}$ is H or alkyl having 1–6 C atoms, but preferably H.

Accordingly, the invention relates in particular to those compounds of the formula I in which at least one of the radicals mentioned has one of the preferred meanings given above. Some preferred groups of compounds can be expressed by the following subformulae Ia to In, which correspond to the formula I and in which the radicals not designated in greater detail have the meaning given in the formula I, but in which in Ia) $R^3$ is H;

in Ib) $R^3$ is H and
$R^2$ is $COOR^{10}$ or $SO_2R^{10}$;

in Ic) $R^3$ is H,
$R^2$ is $COOR^{10}$ or $SO_2R^{10}$ and
$R^{10}$ is H, A, Ar or aralkylene having 7–14 C atoms;

in Id) m is 0;

in Ie) m is 0 and
$R^3$ is H;

in If) $R^3$ is H,
$R^2$ is $COOR^{10}$ or $SO_2R^{10}$ and
m is 0;

in Ig) $R^3$ is H,
$R^2$ is $COOR^{10}$ or $SO_2R^{10}$ and
$R^{10}$ is H, A, Ar or aralkylene with 7–14 C atoms and
m is 0;

in Ih) $R^3$ is H,
$R^2$ is $COOR^{10}$ or $SO_2R^{10}$ and
$R^{10}$ is H, A, Ar or aralkylene having 7–14 C atoms and
A is H or unsubstituted alkyl having 1–15 C atoms or cycloalkyl having 3–15 C atoms,
Ar is phenyl or naphthyl and
m is 0;

in Ii) $R^6$ is a mono- or binuclear heterocycle having 1 to 4 N atoms, which can be unsubstituted or mono-, di- or trisubstituted by Hal, A, —CO-A, OH, CN, COOH, COOA, $CONH_2$, $NO_2$, =NH or =O, in Ij) $R^3$ is H,
$R^2$ is $COOR^{10}$ or $SO_2R^{10}$ and
$R^{10}$ is H, A, Ar or aralkylene having 7–14 C atoms and
m is 0;
$R^6$ is a mono- or binuclear heterocycle having 1 to 4 N atoms, which can be unsubstituted or mono-, di- or trisubstituted by Hal, A, —CO-A, OH, CN, COOH, COOA, $CONH_2$, $NO_2$, =NH or =O, in Ik) Z is absent;

in Il) Z is absent and
$R^3$ is H;

in Im) Z is absent,
$R^3$ is H and
$R^2$ is $COOR^{10}$ or $SO_2R^{10}$, in In) Z is absent,
$R^3$ is H,
$R^4$ is H,
$R^2$ is $COOR^{10}$ or $SO_2R^1$;
$R^{10}$ is H, A, Ar or aralkylene having 7–14 C atoms,
$R^6$ is a mono- or binuclear heterocycle having 1 to 4 N atoms, which can be unsubstituted or mono-, di- or trisubstituted by Hal, A, —CO-A, OH, CN, COOH, COOA, $CONH_2$, $NO_2$, =NH or =O,
A is H or unsubstituted alkyl having 1–6 C atoms,
Ar is phenyl or naphthyl and
m is 0.

Particularly preferred groups of compounds are those below having the formula I given in each case a)

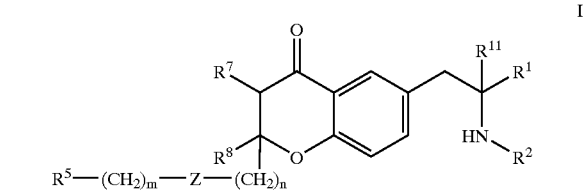

in which
$R^1$ is $CH_2OR^{10}$, $COOR^{10}$ $CONHR^{10}$ or $CON(R^{12})_2$,
$R^2$ is $COOR^{10}$ or $SO_2R^{10}$,
$R^5$ is $NH_2$, $H_2N$—C(=NH) or $H_2N$—(C=NH)—NH or $R^6$—NH—,
$R^6$ is 1H-imidazol-2-yl, 1H-benzimidazol-2-yl, pyrimidin-2-yl or pyridin-2-yl,
$R^7$, $R^8$ in each case independently of one another is absent or is H,
$R^7$ and $R^8$ together are also a bond,
Z is absent,
$R^{10}$ is H, A, Ar or benzyl,
$R^{11}$ is H,
$R^{12}$ is alkyl having 1–6 C atoms,
A is H or unsubstituted alkyl having 1–15 C atoms or cycloalkyl having 3–15 C atoms,
Ar is phenyl or naphthyl,
m is 0,
n is 2, 3 or 4,
and their physiologically acceptable salts and solvates;

b)

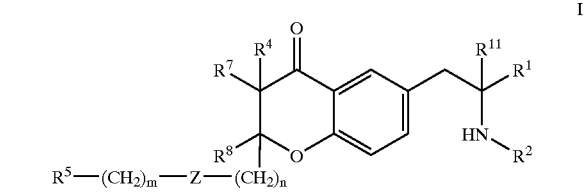

in which
- $R^1$ is $CH_2OR^{10}$ $COOR^{10}$ $CONHR^{10}$ or $CON(R^{12})_2$,
- $R^2$ is $R^{10}$, $CO-R^{10}$, $COOR^{10}$ or $SO_2R^{10}$,
- $R^4$ is H or $R^{12}$,
- $R^5$ is $NH_2$, $H_2N-C(=NH)$ or $H_2N-(C=NH)-NH$, where the primary amino groups can also be provided with conventional amino protective groups, or can be mono-, di- or trisubstituted by $R^{10}$, $CO-R^{10}$, $COOR^{10}$ or $SO_2R^{10}$,
  or $R^6-NH-$,
- $R^6$ is 1H-imidazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyridin-2-yl, pyrimidin-2-yl or 1,4,5,6-tetrahydropyrimidin-2-yl,
- $R^7$, $R^8$ in each case independently of one another is absent or is H,
- $R^7$ and $R^8$ together are also a bond,
- Z is absent,
- $R^{10}$ is H, A, Ar or aralkylene having 7–14 C atoms,
- $R^{11}$ is H,
- $R^{12}$ is alkyl having 1–6 C atoms,
- A is H or unsubstituted alkyl having 1–6 C atoms,
- Ar is phenyl or naphthyl,
- Hal is F, Cl, Br or I and
- m is 0,
- n is 2, 3 or 4, and their physiologically acceptable salts and solvates;

c)

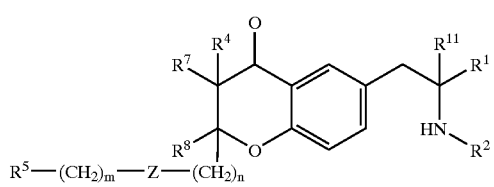

in which
- $R^1$ is $CH_2OR^{10}$, $COOR^{10}$, $CONHR^{10}$ or $CON(R^{12})_2$,
- $R^2$ is $R^{10}$, $CO-R^{10}$, $COOR^{10}$ or $SO_2R^{10}$,
- $R^4$ is H or $R^{12}$,
- $R^5$ is $NH_2$, $H_2N-C(=NH)$ or $H_2N-(C=NH)-NH$, where the primary amino groups can also be provided with conventional amino protective groups, or can be mono-, di- or trisubstituted by $R^{10}$, $CO-R^{10}$, $COOR^{10}$ or $SO_2R^{10}$,
  or $R^6-NH-$
- $R^6$ is 1H-imidazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyridin-2-yl, pyrimidin-2-yl or 1,4,5,6-tetrahydropyrimidin-2-yl,
- $R^7$, $R^8$ in each case independently of one another is absent or is H,
- $R^7$ and $R^8$ together are also a bond,
- Z is absent, O, $C(=O)$ or $CH=CH$,
- $R^9$ is H, Hal, $OR^{11}$, $NH_2$, $NHR^{12}$, $N(R^{12})_2$, NHAcyl, OAcyl, CN, $NO_2$, $SR^{11}$, $SOR^{12}$, $SO_2R^{12}$ or $SO_3H$,
- $R^{10}$ is H, A, Ar or aralkylene having 7–14 C atoms,
- $R^{11}$ is H,
- $R^{12}$ is alkyl having 1–6 C atoms,
- A is H or unsubstituted alkyl having 1–6 C atoms,
- Ar is phenyl or naphthyl which is unsubstituted or is mono-, di- or trisubstituted by A and/or $R^9$,
- Hal is F, Cl, Br or I and
- m is 0,
- n is 2, 3 or 4, and their physiologically acceptable salts and solvates;

d)

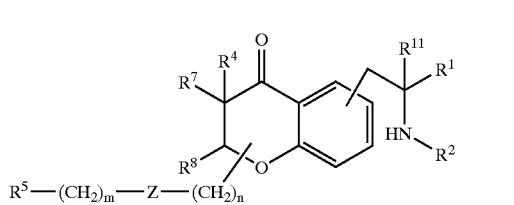

in which
- $R^1$ is $CH_2OR^{10}$ $COOR^{10}$ $CONHR^{10}$ or $CON(R^{12})_2$,
- $R^2$ is $R^{10}$, $CO-R^{10}$, $COOR^{10}$ or $SO_2R^{10}$,
- $R^4$ is H or $R^{12}$,
- $R^5$ is $NH_2$, $H_2N-C(=NH)$ or $H_2N-(C=NH)-NH$, where the primary amino groups can also be provided with conventional amino protective groups, or can be mono-, di- or trisubstituted by $R^{10}$, $CO-R^{10}$, $COOR^{10}$ or $SO_2R^{10}$,
  or $R^6-NH-$,
- $R^6$ is 1H-imidazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyridin-2-yl, pyrimidin-2-yl or 1,4,5,6-tetrahydropyrimidin-2-yl,
- $R^7$, $R^8$ in each case independently of one another is absent or is H,
- $R^7$ and $R^8$ together are also a bond,
- Z is absent,
- $R^9$ is H, Hal, $OR^{11}$, $NH_2$, $NHR^{12}$, $N(R^{12})_2$, NHAcyl, OAcyl, CN, $NO_2$, $SR^{11}SOR^{12}$, $SO_2R^{12}$ or $SO_3H$,
- $R^{10}$ is H, A, Ar or aralkylene having 7–14 C atoms,
- $R^{11}$ is H or alkyl having 1–6 C atoms,
- $R^{12}$ is alkyl having 1–6 C atoms,
- A is H or unsubstituted alkyl having 1–6 C atoms,
- Ar is phenyl or naphthyl which is unsubstituted or mono-, di- or trisubstituted by A, and/or $R^9$,
- Hal is F, Cl, Br or I and
- m is 0,
- n is 1, 2, 3 or 4, and their physiologically acceptable salts and solvates.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, but not mentioned here in greater detail.

If desired, the starting substances can also be formed in situ such that they are not isolated from the reaction mixture, but immediately reacted further to give the compounds of the formula I.

Compounds of the formula I can preferably be obtained by liberating compounds of the formula I from their functional derivatives by treating with a solvolysing or hydrogenolysing agent.

Preferred starting substances for the solvolysis or hydrogenolysis are those which otherwise correspond to the formula I, but instead of one or more free amino and/or hydroxy groups contain corresponding protected amino and/or hydroxy groups, preferably those which, instead of an H atom which is bonded to an N atom, carry an amino protective group, in particular those which, instead of an HN group, carry an R'—N group, in which R' is an amino protective group, and/or those which, instead of the H atom of a hydroxy group, carry a hydroxy protective group, e.g. those which correspond to the formula I, but which instead of a group —COOH carry a group —COOR", in which R" is a hydroxy protective group.

It is also possible for a number of—identical or different—protected amino and/or hydroxy groups to be present in the molecule of the starting substance. If the protective groups present are different from one another, in many cases they can be removed selectively.

The expression "amino protective group" is generally known and relates to groups which are suitable for protecting (or blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1–20, in particular 1–8, C atoms are preferred. The expression "acyl group" is to be interpreted in the widest sense in connection with the present process. It includes acyl groups derived from aliphatic, araliphatic, aromatic or heterocyclic carboxylic acids or sulfonic acids and, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxycarbonyl; aralkyloxycarbonyl such as CBZ ("carbobenzoxy"), 4-methylbenzyloxycarbonyl, FMOC; arylsulfonyl such as Mtr. Preferred amino protective groups are BOC and Mtr, in addition CBZ, Fmoc, benzyl and acetyl.

The removal of the amino protective group is carried out—depending on the protective group used—e.g. using strong acid, expediently using TFA or perchloric acid, but also using other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible., but not always necessary. Suitable inert solvents are preferably organic, for example carboxylic acids such as acetic acid, ethers such as tetrahydrofuran or dioxane, amides such as DMF, halogenated hydrocarbons such as dichloromethane, in addition also alcohols such as methanol, ethanol or isopropanol, as well as water. Mixtures of the abovementioned solvents are furthermore suitable. TFA is preferably used in an excess without addition of a further solvent, perchloric acid in the form of a mixture of acetic acid and 70% perchloric acid in the ratio 9:1. The reaction temperatures for the cleavage are expediently between approximately 0 and approximately 500; the reaction is preferably carried out at between 15 and 300 (room temperature).

The groups BOC, OBut and Mtr can preferably be removed, for example, using TFA in dichloromethane or using approximately 3 to 5N HCl in dioxane at 15–30°, the FMOC group using an approximately 5 to 50% strength solution of dimethylamine, diethylamine or piperidine in DMF at 15–30°.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents here are those indicated above, in particular, for example, alcohols such as methanol or ethanol or amides such as DMF. As a rule, the hydrogenolysis is carried out at temperatures between approximately 0 and 1000 and pressures between approximately 1 and 200 bar, preferably at 20–30° and 1–10 bar. Hydrogenolysis of the CBZ group takes place well, for example, on 5 to 10% Pd/C in methanol or using ammonium formate (instead of hydrogen) on Pd/C in methanol/DMF at 20–30°.

Compounds of the formula I in which $R^5$ is $R^6$—NH— can preferably be obtained, for example, analogously to the reaction schemes 1–3.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane; glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate, water or mixtures of the solvents mentioned.

It is furthermore possible to convert a radical $R^1$, $R^2$ and/or $R^5$ into another radical $R^1$, $R^2$ and/or $R^5$.

In particular, a carboxylic acid ester can be converted into a carboxylic acid.

Thus it is possible to hydrolyse an ester of the formula I. Expediently, this is carried out by solvolysis or hydrogenolysis, as indicated above, e.g. using NaOH or KOH in dioxane/water at temperatures between 0 and 60° C., preferably between 10 and 40° C.

The conversion of a cyano group into an amidino group is carried out by reaction with, for example, hydroxylamine and subsequent reduction of the N-hydroxyamidine with hydrogen in the presence of a catalyst such as, for example, Pd/C.

It is furthermore possible to replace a conventional amino protective group by hydrogen by removing the protective group, as described above, solvolytically or hydrogenolytically or by liberating an amino group protected by a conventional protective group by solvolysis or hydrogenolysis.

For the preparation of compounds of the formula I in which $R^5$ is $H_2N$—C(=NH)—NH—, an appropriate amino compound can be treated with an amidinating agent. A preferred amidinating agent is 1-amidino-3,5-dimethylpyrazole (DPFN), which is particularly employed in the form of its nitrate. The reaction is expediently carried out with addition of a base such as triethylamine or ethyldiisopropylamine in an inert solvent or solvent mixture, e.g. water/dioxane at temperatures between 0 and 120° C., preferably between 60 and 120° C.

For the preparation of an amidine of the formula I ($R^5$=—C(=NH)—$NH_2$), ammonia can be added to a nitrile of the formula I ($R^5$=CN). The addition is preferably carried out in a number of stages by a) converting the nitrile in a manner known per se using $H_2S$ into a thioamide, which is converted using an alkylating agent, e.g. $CH_3I$, into the corresponding S-alkylimidothioester, which for its part reacts with $NH_3$ to give the amidine, b) converting the nitrile using an alcohol, e.g. ethanol in the presence of HCl, into the corresponding imidoester and treating this with ammonia, or c) reacting the nitrile with lithium bis(trimethylsilyl)amide and then hydrolysing the product.

Furthermore, free amino groups can be acylated in the customary manner using an acid chloride or anhydride or alkylated using an unsubstituted or substituted alkyl halide, expediently in an inert solvent such as dichloromethane or THF and/or in the presence of a base such as triethylamine or pyridine at temperatures between −60 and +30°.

A base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, in addition organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, laurylsulfuric acid. Salts with physiologically unacceptable acids, e.g. picrates, can be used for the isolation and/or purification of the compounds of the formula I.

On the other hand, an acid of the formula I can be converted into one of its physiologically acceptable metal or ammonium salts by reaction with a base. Possible salts here are, in particular, the sodium, potassium, magnesium, calcium and ammonium salts, in addition substituted ammonium salts, e.g. the dimethyl-, diethyl- or diisopropylammonium salts, monoethanol-, diethanol- or diisopropylammonium salts, cyclohexyl-, dicyclohexylammonium salts, dibenzylethylenediammonium salts, furthermore, for example, salts with arginine or lysine.

The compounds of the formula I contain one or more chiral centres and can therefore be present in racemic or in optically active form. Racemates obtained can be separated into the enantiomers mechanically or chemically by methods known per se. Preferably, diastereomers are formed from the racemic mixture by reaction with an optically active resolving agent. Suitable resolving agents are, for example, optically active acids, such as the D and L forms of tartaric acid, diacetyltartaric acid, dibenzoyltartaric acid, mandelic acid, malic acid, lactic acid or the various optically active camphorsulfonic acids such as O-camphorsulfonic acid. Resolution of enantiomers with the aid of a column packed with an optically active resolving agent (e.g. dinitrobenzoylphenylglycine) is also advantageous; a suitable eluent is, for example, a mixture of hexane/isopropanol/acetonitrile, e.g. in the volume ratio 82:15:3.

Of course, it is also possible to obtain optically active compounds of the formula I according to the methods described above, by using starting substances which are already optically active.

The invention further relates to the use of the compounds of the formula I and/or their physiologically acceptable salts for the production of pharmaceutical preparations, in particular in a non-chemical manner in this context, they can be brought into a suitable dose form together with at least one solid, liquid and/or semi-liquid vehicle or excipient and, if appropriate, in combination with one or more further active compounds.

The invention further relates to pharmaceutical preparations comprising at least one compound of the formula I and/or one of its physiologically acceptable salts.

These preparations can be used as medicaments in human or veterinary medicine. Suitable vehicles are organic or inorganic substances which are suitable for enteral (e.g. oral) or parenteral administration or topical application or for application in the form of an inhalation spray and do not react with the novel compounds, for example water, vegetable oils, benzyl alcohols, alkylene glycols, polyethylene glycols, glycerol triacetate, gelatin, carbohydrates such as lactose or starch, magnesium stearate, talc, petroleum jelly. Tablets, pills, coated tablets, capsules, powders, granules, syrups, juices or drops are used for oral administration, suppositories are used, in particular, for rectal administration, solutions, preferably oily or aqueous solutions, in addition suspensions, emulsions or implants, are used for parenteral administration and ointments, creams or powders are used for topical application. The novel compounds can also be lyophilized and the lyophilizates obtained used, for example, for the production of injection preparations. The preparations indicated can be sterilized and/or can contain excipients such as glidants, preservatives, stabilizing and/or wetting agents, emulsifiers, salts for affecting the osmotic pressure, buffer substances, colourants, flavourings and/or [lacuna] more further active compounds, e.g. one or more vitamins.

For administration as an inhalation spray, sprays can be used which contain the active compound either dissolved or suspended in a propellant or propellant mixture (e.g. $CO_2$ or chlorofluorohydrocarbons). Expediently, the active compound is used here in micronized form, it being possible for one or more additional physiologically tolerable solvents to be present, e.g. ethanol. Inhalation solutions can be administered with the aid of customary inhalers.

The invention also relates to the use of the compounds of the formula I as therapeutic active compounds.

The compounds of the formula I and their physiologically acceptable salts can be used as integrin inhibitors in the control of diseases, in particular of pathological angiogenic disorders, thromboses, cardiac infarct, coronary heart disorders, arteriosclerosis, tumours, inflammations and infections.

In this context, the substances according to the invention can as a rule be administered in analogy to other known commercially available peptides, but in particular in analogy to the compounds described in U.S. Pat. No. 4,472,305, preferably in doses between approximately 0.05 and 500 mg, in particular between 0.5 and 100 mg, per dose unit. The daily dose is preferably between approximately 0.01 and 2 mg/kg of body weight. The specific dose for each patient depends, however, on all sorts of factors, for example on the efficacy of the specific compound employed, on the age, body weight, general state of health and sex, on the diet, on the time and route of administration, and on the excretion rate, pharmaceutical combination and severity of the particular disorder to which the therapy applies. Parenteral administration is preferred.

Above and below, all temperatures are given in °C. In the following examples, "customary working up" means: if necessary, water is added, the pH is adjusted, if necessary, depending on the constitution of the final product, to a pH of between 2 and 10, the mixture is extracted with ethyl acetate or dichloromethane, the organic phase is separated off, dried over sodium sulfate and evaporated, and the residue is purified by chromatography on silica gel and/or by crystallization.

Mass spectrometry (MS): EI (electron impact ionization) M$^+$
FAB (from FAB (fast atom bombardment) (M+H)$^+$

EXAMPLE 1

(2S)-3-{2-[3-1H-Imidazol-2-ylamino)propyl]-4-oxo-4H-chromen-6-yl}-2-(2,2-dimethylpropoxycarboxamido)propionic acid The synthesis of the compound is carried out, for example, as indicated in Scheme 1.

80 g (0.31 mol) of 3-acetyl-L-tyrosine are suspended in 1 l of anhydrous ethanol and the mixture is refluxed at 80° C. for 12 h in the presence of 70 g (0.37 mol) of toluene-4-sulfonic acid. After cooling to RT, 500 ml of MTB ether are added, and the precipitated crystals are filtered off with suction and washed with MTB ether and dried.

Yield: 99.4 g of 3-acetyl-L-tyrosine ethyl ester ("AB") as the pTSS salt.

20 g (47.2 mmol) of "AB", are suspended in 320 ml of water and 160 ml of THF and treated in portions with 8 g (94 mmol) of NaHCO$_3$ with stirring. A solution of 8.6 g (56 mmol) of neopentyl chloroformate in 160 ml of THF is then added dropwise and the mixture is stirred at RT for 30 min and worked up in the customary manner. The residue is recrystallized from MTB ether.

Yield: 16.1 g (93%) of N-(2,2-dimethylpropyloxycarbonyl)-3-acetyl-L-tyrosine ethyl ester ("AC").

5 g (14.2 mmol) of "AC" and 3.3 g (17 mmol) of 4-benzyloxybutyric acid are dissolved in 100 ml of DMF and treated at RT with 3.1 ml (28.4 mmol) of N-methylmorpholine and 4.08 g (21.3 mmol) of EDCI. After 5 h, the reaction solution is added to 700 ml of water and worked up in the customary manner.

Yield: 7.4 g of (2-acetyl-4-(2-carboxyethyl-2-(2,2-dimethylpropyl)oxycarbonylaminoethyl)phenyl 4-benzyloxybutyrate ester "AD".

6.2 g (11.4 mmol) of "AD" are dissolved in 100 ml of anhydrous THF and stirred with 342 mg (11.4 mmol) of sodium hydride (80% in mineral oil) at RT. After 30 min, the solution is neutralized with acidic ion exchanger and concentrated.

Yield: 6.2 g of ethyl (2S)-3-(2-hydroxy-2-(3-benzyloxypropyl)-4-oxochroman-6-yl)-2-(2,2-dimethylpropyl)oxycarbonylaminopropionate ("AE").

18 ml of trifluoroacetic acid are added to a solution of 6.2 g (11.4 mmol) of "AE" in 180 ml of dichloromethane and the mixture is stirred overnight at RT. The solution is then concentrated, concentrated a further 3 times using 50 ml of toluene each time and the residue chromatographed on silica gel using toluene/methanol 20/1 as eluent.

Yield: 4.2 g of ethyl (2S)-3-(2-(3-benzyloxypropyl)-4-oxo-4H-chromen-6-yl)-2-(2,2-dimethylpropyl)oxycarbonylaminopropionate ("AF"), FAB 534.

3.5 g (6.7 mmol) of "AF" are hydrogenated at RT under normal pressure for 1 h in 50 ml of ethanol in the presence of 350 mg of palladium (10% on active carbon). After filtering off the catalyst and concentrating the solution, the product is obtained as a colourless, amorphous mass.

Yield: 2.6 g of ethyl (2S)-3-(2-(3-hydroxypropyl)-4-oxo-4H-chromen-6-yl)-2-(2,2-dimethylpropyl) oxycarbonylaminopropionate ("AG"), FAB 434.

0.267 ml (1.72 mmol) of DEAD (diethyl azodicarboxylate) and 450 mg (172 mmol) of triphenylphosphine are added to a solution of 500 mg of (1.15 mmol) of "AG" and 357 mg (1.38 mmol) of 2-(2,2,2-trichlorethoxycarbonyl)amino-1H-imidazole in 20 ml of anhydrous THF and the mixture is stirred overnight at 60° C. The solution is then concentrated and the residue is chromatographed on silica gel RP-8 using methanol/water 2:1.

Yield: 560 mg of ethyl (2S)-3-(2-(3-((1H-imidazol-2-yl)-(2,2,2-trichloroethoxycarbonyl)amino)propyl)-4-oxo-4H-chromen-6-yl)-2-(2,2-dimethylpropyl) oxycarbonylaminopropionate ("AH") as a colourless oil, FAB 675.

A solution of 280 mg (4.15 mmol) of "AH" in 5 ml of THF with 0.5 ml of acetic acid and 0.5 ml of water is treated with 500 mg (7.7 mmol) of zinc dust and stirred at RT for 1 h. Solid is then filtered off, the solution is concentrated and the residue is dried.

Yield: 210 mg of ethyl (2S)-3-{2-[3-(1H-imidazol-2-ylamino)propyl]-4-oxo-4H-chromen-6-yl}-2-(2,2-dimethylpropoxycarboxamido)propionate ("AI"), FAB 499.

200 mg (0.4 mmol) of "AI" are dissolved in 4 ml of dioxane and stirred at 75° C. for 12 h with 2 ml of 1N HCl. The solution is concentrated and the residue is purified by preparative HPLC on RP-18 silica gel using an eluent gradient (water/acetonitrile 99:1 to 1:99 in 60 min). The product is obtained after freeze-drying of the HPLC fractions as a white, amorphous powder.

Yield: 103 mg of (2S)-3-{2-[3-(1H-imidazol-2-ylamino) propyl]-4-oxo-4H-chromen-6-yl}-2-(2,2-dimethylpropoxycarboxamido)propionic acid ("AK"), m.p. 105–1100; FAB 471.

Scheme 1:

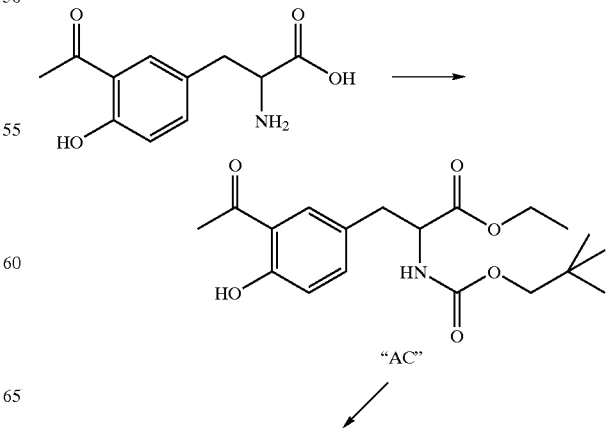

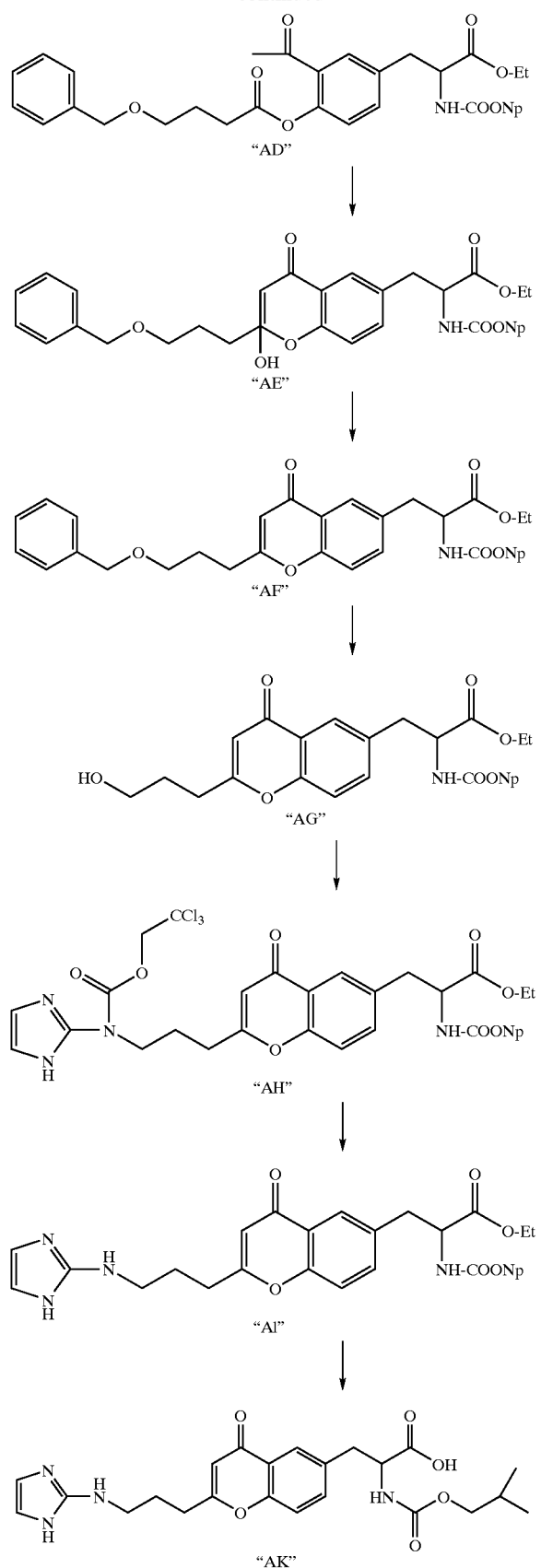

EXAMPLE 2

(2S)-3-{2-[3-(Pyridin-2-ylamino)propyl]-4-oxo-4H-chromen-6-yl}-2-(2,2-dimethylpropoxycarboxamido)propionic acid The synthesis of the compound is carried out, for example, as indicated in Scheme 2.

A solution of 0.5 g (1.37 mmol) of "AC" and 630 mg (1.77 mmol) of 4-(pyridin-2-yl-(2,2,2-trichlorethoxycarbonyl)amino)butyric acid in 10 ml of dichloromethane is treated at RT with 420 mg (2.04 mmol) of DCC and 20 mg of DMAP and stirred for 15 h. The precipitated dicyclohexylurea is then filtered off, the residue is washed with dichloromethane and the solution is concentrated. The residue is chromatographed on silica gel using toluene/acetone 20:1.

Yield: 130 mg of (2-acetyl-4-(2-carboxyethyl-2-(2,2-dimethylpropyl)oxycarbonyl amino ethyl)phenyl 4-(pyridin-2-yl-(2,2,2-trichlorethoxycarbonyl)amino) butyrate ("BB"), FAB 704.

130 mg (0.185 mmol) of "BB" are reacted at RT with 5.4 mg (0.18 mmol) of sodium hydride (80% in mineral oil) in 5 ml of THF. After 45 min, the mixture is neutralized with acetic acid and concentrated to give a residue.

Yield: 130 mg of ethyl (2S)-3-(2-hydroxy-2-(3-(pyridin-2-yl-(2,2,2-trichloroethoxycarbonyl)amino)propyl)-4-oxochroman-6-yl)-2-(2,2-dimethylpropyl)oxycarbonylaminopropionate ("BC").

130 mg (0.18 mmol) of "BC" are stirred at RT for 15 h in 5 ml of dichloromethane and 0.5 ml of trifluoroacetic acid. The solution is then concentrated and the residue is chromatographed on silica gel.

Yield: 55 mg of ethyl (2S)-3-(2-(3-((pyridin-2-yl)-(2,2,2-trichloroethoxycarbonyl)amino)propyl)-4-oxo-4H-chromen-6-yl)-2-(2,2-dimethylpropyl)oxycarbonylaminopropionate ("BD) FAB 686.

The removal of the TROC group from "BD" a is carried out analogously to "AI" and gives, after working up, 40 mg of ethyl (2S)-3-{2-[3-(pyridin-2-ylamino)propyl]-4-oxo 4H-chromen-6-yl}-2-(2,2-dimethylpropoxycarboxamido)propionate ("BE").

40 mg (78 μmol) of "BE" are stirred at 70° C. for 60 h in 2 ml of dioxane with 1 ml of 1N HCl. After concentration, the residue is purified by prep. HPLC on RP-18 silica gel.

Yield: 20 mg of (2S)-3-{2-[3-(pyridin-2-ylamino)propyl]-4-oxo-4H-chromen-6-yl}-2-(2,2-dimethylpropoxycarboxamido)propionic acid ("BF") as a white, amorphous powder after freeze-drying, m.p. 80–85°, FAB 482.

Scheme 2:

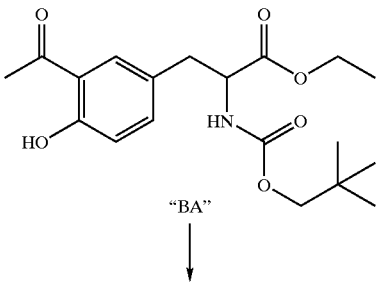

"BA"

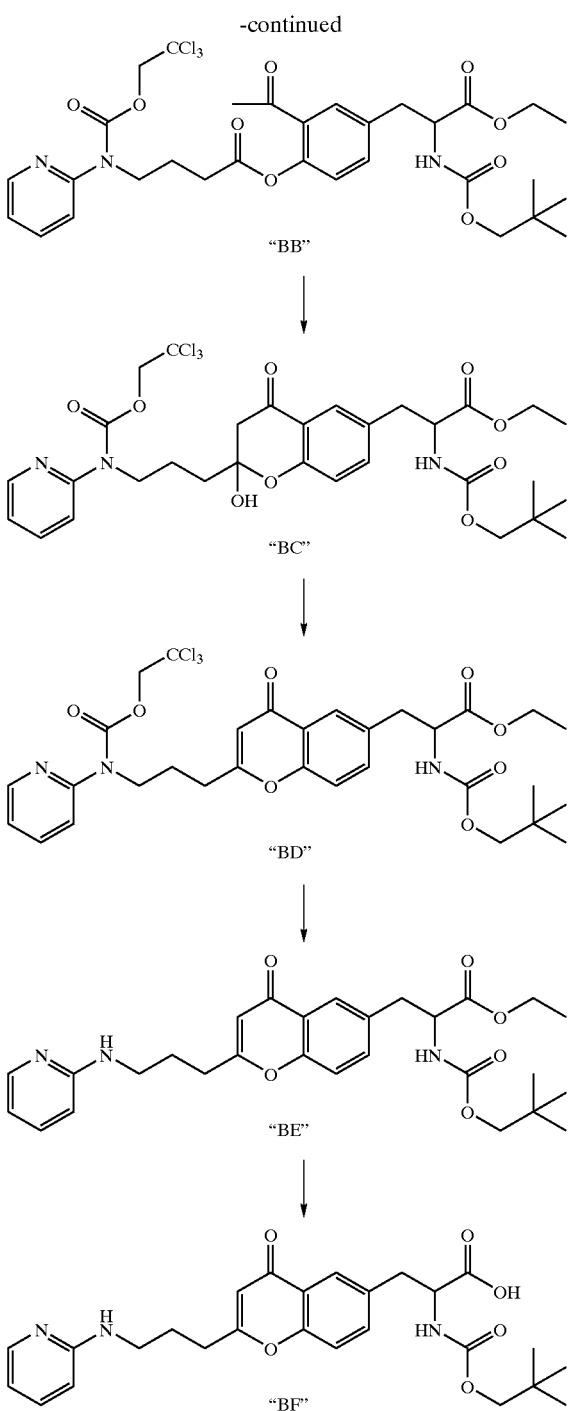

purified by chromatography on silica gel using 15 toluene/acetone 6:1 as an eluent.

Yield: 7.7 g of (2-acetyl-4-(2-carboxyethyl-2-(2,2-dimethylpropyl)oxycarbonylaminoethyl)phenyl 4-acetoxybutyrate ("CA") as a colourless oil, FAB 494.

Corresponding to Example 1, 7.7 g (15.7 mmol) of "CA" are reacted at RT for 16 h with 489 mg (16.3 mmol) of NaH (80% in mineral oil) in 200 ml of THF and the mixture is worked up.

Yield: 7.2 g of ethyl (2S)-3-(2-hydroxy-2-(3-acetoxypropyl)-4-oxochroman-6-yl)-2-(2,2-dimethylpropyl)oxycarbonylaminopropionate ("CB") as a crude product which is reacted further without purification.

Analogously to Example 1, the dehydration of 7.2 g (15.7 mmol) of "CB" using 18 ml of trifluoroacetic-acid in 180 ml of dichloromethane proceeds in 48 h at RT. The crude product obtained after concentration of the reaction solution is dried and directly reacted further.

Yield: 7.0 g of ethyl (2S)-3-(2-(3-acetoxypropyl)-4-oxo-4H-chromen-6-yl)-2-(2,2-dimethylpropyl) oxycarbonylaminopropionate ("CC") as a colourless oil.

7.0 g (14.7 mmol) of "CC" are stirred at RT for 1 h in 200 ml of anhydrous ethanol with 1.9 g (28 mmol) of sodium ethoxide. The mixture is then neutralized using acidic ion exchanger, and the solution is concentrated to give a residue and chromatographed on silica gel using toluene/acetone 2:1.

Yield: 2.4 g of ethyl (2S)-3-(2-(3-hydroxypropyl)-4-oxo-4H-chromen-6-yl)-2-(2,2-dimethylpropyl) oxycarbonylaminopropionate ("CD"), FAB 434.

500 mg (1.15 mmol) of "CD" are dissolved in 20 ml of dichloromethane and oxidized at RT for 1.5 h using 370 mg (1.73 mmol) of pyridinium chlorochromate. The reaction solution is filtered through 30 g of silica gel, the filter cake is washed with ethyl acetate and the solution is concentrated. The crude product is reacted without further purification.

Yield: 392 mg of ethyl (2S)-3-(2-(3-oxopropyl)-4-oxo-4H-chromen-6-yl)-2-(2,2-dimethylpropyl) oxycarbonylaminopropionate ("CE").

The crude product "CE" (100 mg, 0.23 mmol) is dissolved in 10 ml of pyridine and reacted with 33 mg (0.25 mmol) of 2-aminobenzimidazole in the presence of 0.13 ml (0.93 mmol) of triethylamine. After reaction is complete (3 h at RT), 18 mg (0.46 mmol) of sodium borohydride are added and the mixture is stirred at RT for a further 3 h. It is then neutralized with dil. acetic acid, the solution is concentrated and the residue is purified by prep. HPLC on RP-18.

Yield: 64 mg of ethyl (2S)-3-{2-[3-(1H-benzimidazol-2-ylamino)propyl]-4-oxo-4H-chromen-6-yl}-2-(2,2-dimethylpropoxycarboxamido)propionic ("CF") as a colourless amorphous powder after freeze-drying, FAB 549.

50 mg (0.09 mmol) of "CF" are stirred with 1 ml of 1N HCl at 80° C. for 12 h in 2 ml of dioxane and the mixture is then concentrated.

EXAMPLE 3

(2S)-3-(2-[3-(1H-Benzimidazol-2-ylamino)propyl]-4-oxo-4H-chromen-6-yl)-2-(2,2-dimethylpropoxycarboxamido)propionic acid The synthesis of the compound is carried out, for example, as indicated in Scheme 3.

6.5 g (17.8 mmol) of "AD" are reacted with 5.2 g (35.6 mmol) of 4-acetoxybutyric acid in the presence of 7.5 g (39.1 mmol) of EDCI and 5.9 ml (53.6 mmol) of NMP in 100 ml of DMF analogously to Example 1. The product is Yield: 45 mg of (2S)-3-{2-[3-(1H-benzimidazol-2-ylamino)propyl]-4-oxo-4H-chromen-6-yl}-2-(2,2-dimethylpropoxycarboxamido)propionic acid ("CG"), FAB 521.
Scheme 3:
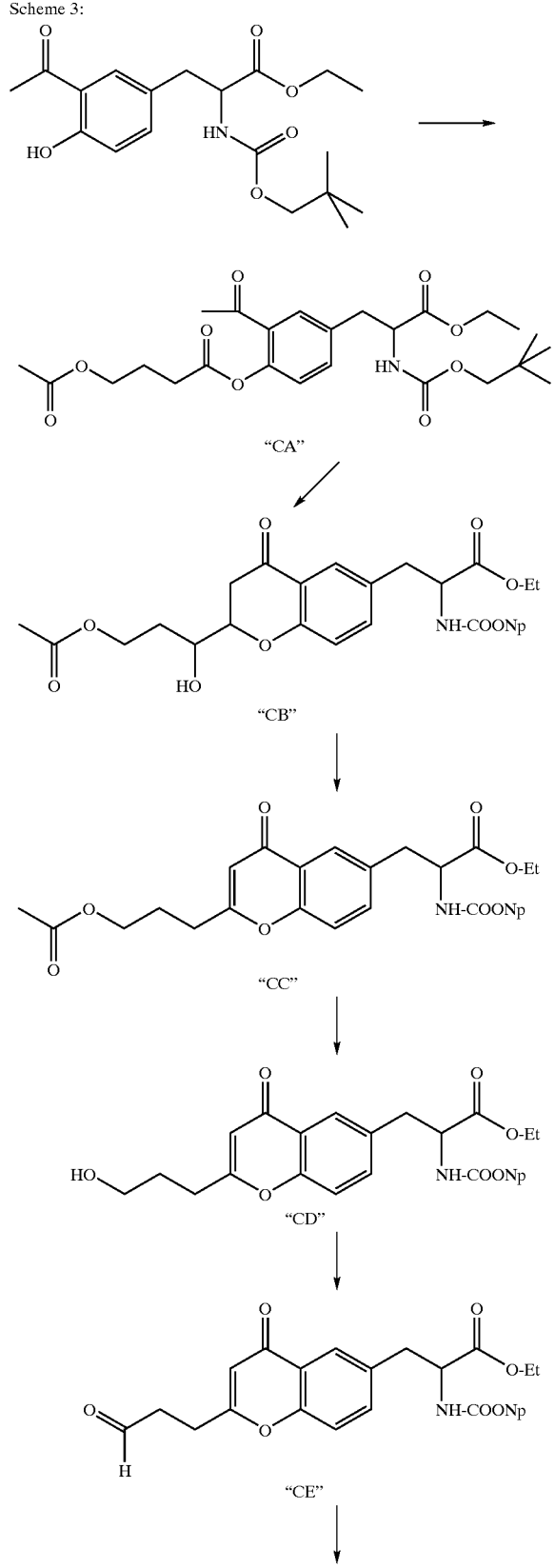
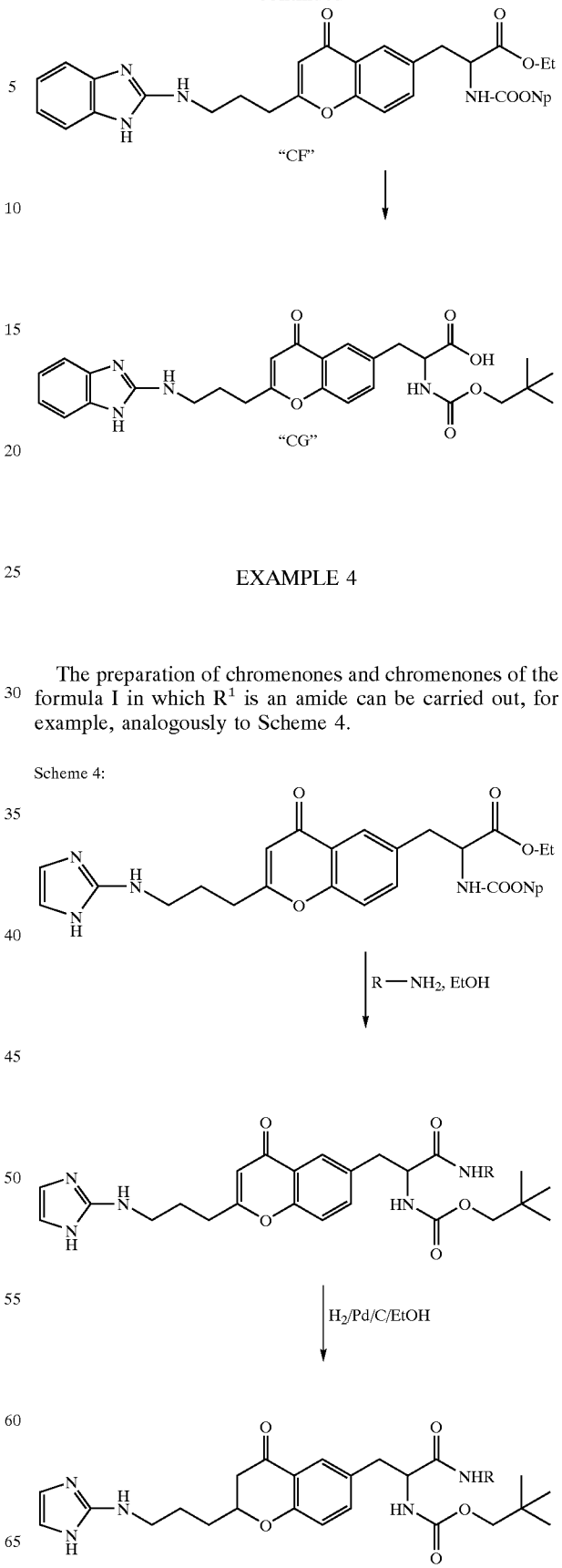
EXAMPLE 4
The preparation of chromenones and chromenones of the formula I in which $R^1$ is an amide can be carried out, for example, analogously to Scheme 4.
Scheme 4:
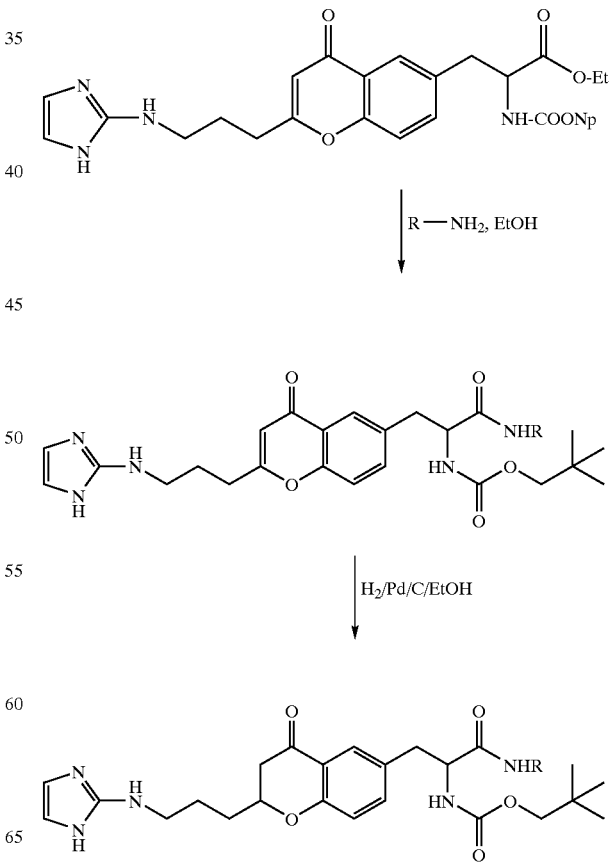

EXAMPLE 5

The preparation of chromenones of the formula I in which $R^1$ is $CH_2OH$ can be carried out, for example, analogously to Scheme 5.

Scheme 5:

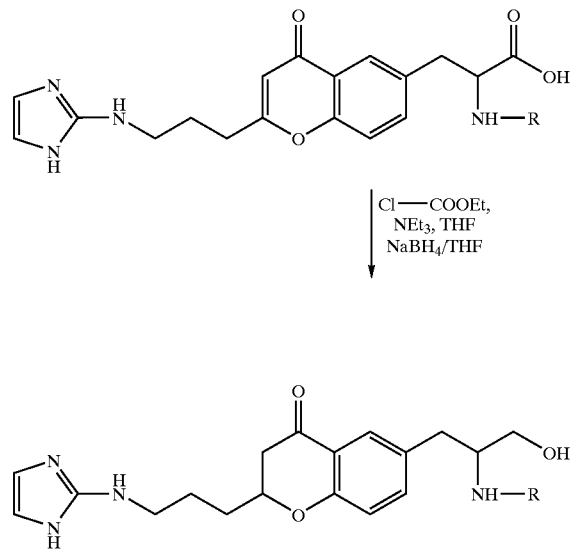

EXAMPLE 6

The preparation of chromenones of the formula I in which $R^5$ is a guanidino group can be carried out, for example, analogously to Scheme 6.

Scheme 6:

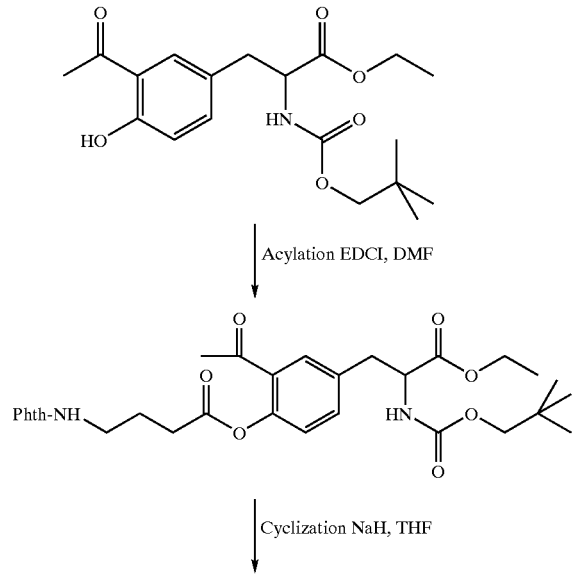

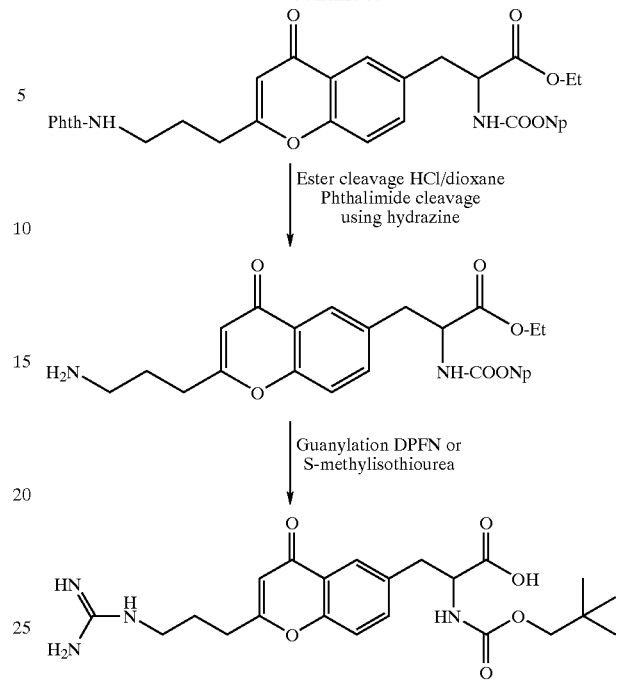

EXAMPLE 7

The preparation of chromenones of the formula I in which $R^5$ is an amidino group can be carried out, for example, analogously to Scheme 7.

Scheme 7:

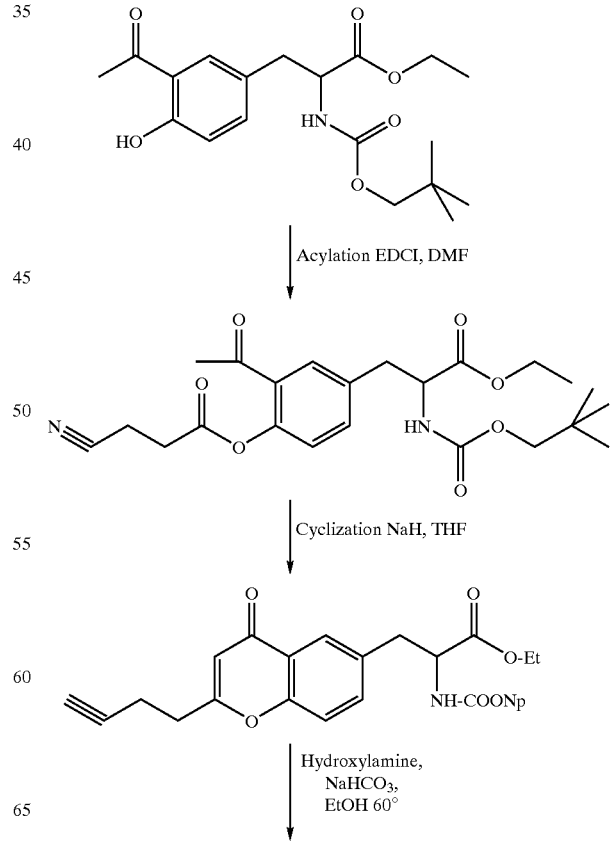

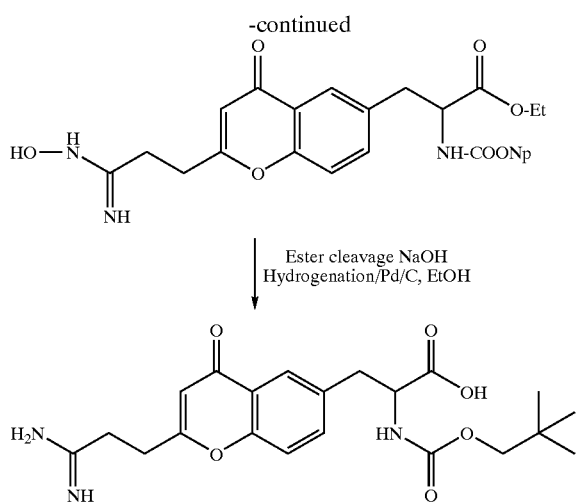

EXAMPLE 8

The sulfonamide derivatives below are obtained analogously to Examples 1, 2 and 3

(2S)-3-{2-[3-(1H-imidazol-2-ylamino)propyl]-4-oxo-4H-chromen-6-yl}-2-(2,2-dimethylpropylsulfonamido)propionic acid, (2S)-3-{2-[3-(pyridin-2-ylamino)propyl]-4-oxo-4H-chromen-6-yl}-2-(2,2-dimethylpropylsulfonamido)propionic acid, (2S)-3-{2-[3-(1H-benzimidazol-2-ylamino)propyl]-4-oxo-4H-chromen-6-yl}-2-(2,2-dimethylpropylsulfonamido)propionic acid, (2S)-3-{2-[3-(1H-imidazol-2-ylamino)propyl]-4-oxo-4H-chromen-6-yl}-2-butylsulfonamidopropionic acid, (2S)-3-{2-[3-(pyridin-2-ylamino)propyl]-4-oxo-4H-chromen-6-yl}-2-butylsulfonamidopropionic acid, (2S)-3-{2-[3-(1H-benzimidazol-2-ylamino)propyl]-4-oxo-4H-chromen-6-yl}-2-butylsulfonamidopropionic acid, (2S)-3-{2-[3-(1H-imidazol-2-ylamino)propyl]-4-oxo-4H-chromen-6-yl}-2-phenylsulfonamidopropionic acid, (2S)-3-{2-[3-(pyridin-2-ylamino)propyl]-4-oxo-4H-chromen-6-yl}-2-phenylsulfonamidopropionic acid, (2S)-3-{2-[3-(1H-benzimidazol-2-ylamino)propyl]-4-oxo-4H-chromen-6-yl}-2-phenylsulfonamidopropionic acid, (2S)-3-{2-[3-(1H-imidazol-2-ylamino)propyl]-4-oxo-4H-chromen-6-yl}-2-benzylsulfonamidopropionic acid, (2S)-3-{2-[3-(pyridin-2-ylamino)propyl]-4-oxo-4H-chromen-6-yl}-2-benzylsulfonamidopropionic acid, (2S)-3-{2-[3-(1H-Benzimidazol-2-ylamino)propyl]-4-oxo-4H-chromen-6-yl}-2-benzylsulfonamidopropionic acid.

The following examples relate to pharmaceutical preparations:

EXAMPLE A: INJECTION VIALS

A solution of 100 g of an active compound of the formula 1 and 5 g of disodium hydrogenphosphate is adjusted to pH 6.5 in 3 l of double-distilled water using 2 N hydrochloric acid, sterile-filtered, filled into injection vials, lyophilized under sterile conditions and aseptically sealed. Each injection vial contains 5 mg of active compound.

EXAMPLE B: SUPPOSITORIES

A mixture of 20 g of an active compound of the formula I is fused with 100 g of soyalecithin and 1400 g of cocoa butter, poured into moulds and allowed to cool. Each suppository contains 20 mg of active compound.

EXAMPLE C: SOLUTION

A solution is prepared from 1 g of an active compound of the formula I, 9.38 g of $NaH_2PO_4.2H_2O$, 28.48 g of $Na_2HPO_4 \cdot 12H_2O$ and 0.1 g of benzalkonium chloride in 940 ml of double-distilled water. The solution is adjusted to pH 6.8, made up to 1 1 and sterilized by irradiation. This solution can be used in the form of eye drops.

EXAMPLE D: OINTMENT 500 mg of an active compound of the formula I is mixed with 99.5 g of petroleum jelly under aseptic conditions.

EXAMPLE E: TABLETS

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

EXAMPLE F: COATED TABLETS

Analogously to Example E, tablets are pressed and are then coated in a customary manner with a coating of sucrose, potato starch, talc, tragacanth and colourant.

EXAMPLE G: CAPSULES 2 kg of active compound of the formula I are filled into hard gelatin capsules in a customary manner such that each capsule contains 20 mg of the active compound.

EXAMPLE H: AMPOULES

A solution of 1 kg of active compound of the formula I in 60 l of double-distilled water is sterile-filtered, filled into ampoules, lyophilized under sterile conditions and aseptically sealed. Each ampoule contains 10 mg of active compound.

EXAMPLE I: INHALATION SPRAY 14 g of active compound of the formula I are dissolved in 10 l of isotonic NaCl solution and the solution is filled into commercially available spray containers having a pump mechanism. The solution can be sprayed into the mouth or nose. One puff of spray (approximately 0.1 ml) corresponds to a dose of approximately 0.14 mg.

What is claimed is:

1. A compound of formula I

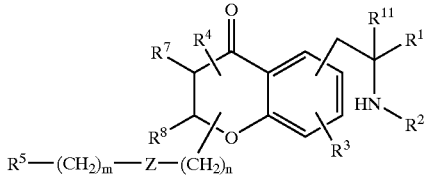

in which $R^1$ is $CH_2OR^{10}$, $COOR^{10}$, $CONHR^{10}$ or $CON(R^{12})_2$, $R^2$ is $R^{10}$, $CO-R^{10}$, $CO-R^6$, $COOR^6$, $COOR^{10}$, $SO_2R^6$, $SO_2R^{10}$, $CONHR^6$, $CON(R^6)_2$, $CONHR^{10}$ or $CON(R^{12})_2$, $R^3$ is H, Hal, $NHR^{10}$, $N(R^{12})_2$, —NH-acyl, —O-acyl, CN, $NO_2$, $OR^{10}$, $SR^{10}$, $SO_2R^{10}$, $SO_3R^{10}$, $COOR^{10}$, $CONHR^6$, $CON(R^6)_2$, $CONHR^{10}$ or $CON(R^{12})_2$, $R^4$ is H, A, Ar or aralkylene having 7–14 C atoms, $R^5$ is $NH_2$, $H_2N—C(=NH)$ or $H_2N—(C=NH)—NH$, where the primary amino groups can also be provided with conventional amino protective groups, or can be mono- di- or trisubstituted by $R^{10}$, $CO—R^{10}$, $COOR^{10}$ or $SO_2R^{10}$, or $R^6—NH—$, $R^6$ is a mono- or binuclear heterocycle having 1 to 4 N, O and/or S atoms, which can be unsubstituted or mono-, di- or trisubstituted by Hal, A, —CO-A, OH, CN, COOH, COOA, $CONH_2$, $NO_2$, $=NH$ or $=O$, $R^7$, $R^8$ in each case independently of one another is H or together form another bond on the ring such that a double bond is formed, Z is absent, O, S, NH, $NR^1$, $C(=O)$, CONH, NHCO, $C(=S)NH$, $NHC(=S)$, $C(=S)$, $SO_2NH$, $NHSO_2$ or $CA=CA'$, $R^9$ is H, Hal, $OR^{11}$, $NH_2$, $NHR^{12}$, $N(R^{12})_2$, NHAcyl, OAcyl, CN, $NO_2$, $SR^{11}$, $SOR^{12}$, $SO_2R^{12}$ or $SO_3H$, $R^{10}$ is H, A, Ar or aralkylene having 7–14 C atoms, $R^{11}$ is H or alkyl with 1–6 C atoms, $R^{12}$ is alkyl having 1–6 C atoms, A is H or alkyl having 1–15 C atoms or cycloalkyl having 3–15 C atoms, which is unsubstituted or is mono-, di- or trisubstituted by $R^9$ and in which one, two or three methylene groups can also be replaced by N, O and/or S, Ar is a mono- or binuclear aromatic ring system having 0, 1, 2, 3 or 4 N, O and/or S atoms, which is unsubstituted or mono-, di- or trisubstituted by A and/or $R^9$, Hal is F, Cl, Br or I, m, n in each case independently of one another are 0, 1, 2, 3 or 4, or a physiologically acceptable salt or solvate or enantiomer or diastereomer thereof.

2. An enantiomer or a diastereomer of the compound of claim 1.

3. A compound of claim 1 selected from the group consisting of
a) (2S)-3-[2-(3-aminopropyl)-4-oxo-4H-chromen-6-yl]-2-(2,2-dimethylpropoxycarboxamido)propionic acid;
b) (2S)-3-{2-[3-(1H-imidazol-2-ylamino)propel]-4-oxo-4H-chromen-6-yl}-2-(2,2-dimethylpropoxycarboxamido) propionic acid;
c) (2S)-3-{2-[3-(1H-imidazol-2-ylamino)propel]-4-oxochroman-6-yl}-2-(2,2-dimethylpropoxycarboxamido) propionic acid;
d) (2S)-3-{2-[3-(pyridin-2-ylamino)propyl]-4-oxo-4H-chromen-6-yl}-2-(2,2-dimethylpropoxycarboxamido) propionic acid;
e) (2S)-3-{2-[3-(1H-benzimidazol-2-ylamino)propyl]-4-oxo-4H-chromen-6-yl}-2-(2,2dimethylpropoxycarboxamido)propionic acid;
or a physiologically acceptable salt or solvate thereof.

4. A process for the preparation of the compound of claim 1, or a physiologically acceptable salt or solvate thereof, wherein
a) a compound of formula I is liberated from one of its functional derivatives by treating with a solvolysing or hydrogenolysing agent, or
b) a radical $R^1$, $R^2$ and/or $R^5$ is converted into another radical $R^1$, $R^2$ and/or $R^5$,
by,
i) converting an amino group into a guanidino group by reaction with an amidinating agent,
ii) hydrolysing an ester,
iii) reducing a carboxylic acid to an alcohol, or
iv) converting a hydroxyamidine into an amidine by hydrogenation and/or converting a base or acid of the formula I into one of its salts.

5. A pharmaceutical composition comprising at least one compound of claim 1 or a physiologically acceptable salt or solvate thereof.

6. A method of treating a disease or condition, said disease or condition is a pathological angiogenic disorder, thrombosis, cardiac infarct, a coronary heart disorder, arteriosclerosis, tumor metastasis, osteoporosis or rheumatoid arthritis comprising administering to a patient in need thereof an effective amount of a composition of claim 5.

7. The compound of claim 1, wherein $R^3$ is H.

8. The compound of claim 1, wherein $R^3$ is H and $R^2$ is $COOR^{10}$ or $SO_2R^{10}$.

9. The compound of claim 1, wherein $R^3$ is H, $R^2$ is $COOR^{10}$ or $SO_2R^{10}$ and $R^{10}$ is H, A, Ar or aralkylene having 7–14 C atoms.

10. The compound of claim 1, wherein m is 0.

11. The compound of claim 1, wherein m is 0 and $R^3$ is H.

12. The compound of claim 1, wherein $R^3$ is H, $R^2$ is $COOR^{10}$ or $SO_2R^{10}$ and m is 0.

13. The compound of claim 1, wherein $R^3$ is H, $R^2$ is $COOR^{10}$ or $SO_2R^{10}$ and $R^{10}$ is H, A, Ar or aralkylene with 7–14 C atoms and m is 0.

14. The compound of claim 1, wherein in $R^3$ is H, $R^2$ is $COOR^{10}$ or $SO_2R^{10}$ and $R^{10}$ is H, A, Ar or aralkylene having 7–14 C atoms and A is H or unsubstituted alkyl having 1–15 C atoms or cycloalkyl having 3–15 C atoms, Ar is phenyl or naphthyl and m is 0.

15. The compound of claim 1, wherein $R^6$ is a mono- or binuclear heterocycle having 1 to 4 N atoms, which can be unsubstituted or mono-, di- or trisubstituted by Hal, A, —CO-A, OH, CN, COOH, COOA, $CONH_2$, $NO_2$, $=NH$ or $=O$.

16. The compound of claim 1, wherein $R^3$ is H, $R^2$ is $COOR^{10}$ or $SO_2R^{10}$ and $R^{10}$ is H, A, Ar or aralkylene having 7–14 C atoms and m is 0, and $R^6$ is a mono- or binuclear heterocycle having 1 to 4 N atoms, which can be unsubstituted or mono-, di- or trisubstituted by Hal, A, —CO-A, OH, CN, COOH, COOA, $CONH_2$, $NO_2$, $=NH$ or $=O$.

17. The compound of claim 1, wherein Z is absent.

18. The compound of claim 1, wherein Z is absent and $R^3$ is H.

19. The compound of claim 1, wherein Z is absent, $R^3$ is H and $R^2$ is $COOR^{10}$ or $SO_2R^{10}$.

20. The compound of claim 1, wherein Z is absent, $R^3$ is H, $R^4$ is H, $R^2$ is $COOR^{10}$ or $SO_2R^{10}$, $R^{10}$ is H, A, Ar or aralkylene having 7–14 C atoms, $R^6$ is a mono- or binuclear heterocycle having 1 to 4 N atoms, which can be unsubstituted or mono-, di- or trisubstituted by Hal, A, —CO-A, OH, CN, COOH, COOA, $CONH_2$, $NO_2$, $=NH$ or $=O$, A is H or unsubstituted alkyl having 1–6 C atoms, Ar is phenyl or naphthyl and m is 0.

21. A compound of formula I

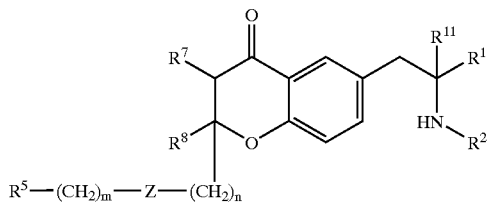

in which
R¹ is CH₂OR¹⁰, COOR¹⁰, CONHR¹⁰ or CON(R¹²)₂,
R² is COOR¹⁰ or SO₂R¹⁰,
R⁵ is NH₂, H₂N—C(=NH) or H₂N—(C=NH)—NH or R⁶—NH—,
R⁶ is 1H-imidazol-2-yl, 1H-benzimidazol-2-yl, pyrimidin-2-yl or pyridin-2-yl,
R⁷, R⁸ in each case independently of one another is H or R⁷ and R⁸ together form a bond,
Z is absent,
R¹⁰ is H, A, Ar or benzyl,
R¹¹ is H,
R¹² is alkyl having 1–6 C atoms,
A is H or unsubstituted alkyl having 1–15 C atoms or cycloalkyl having 3–15 C atoms,
Ar is phenyl or naphthyl,
m is 0,
n is 2, 3 or 4,
or a physiologically acceptable salt or solvate thereof.

22. A compound of formula I

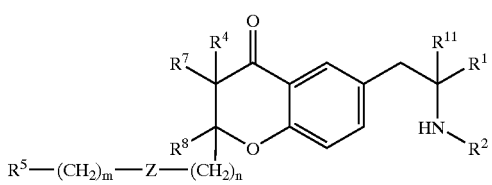

in which
R¹ is CH₂OR¹⁰, COOR¹⁰, CONHR¹⁰ or CON(R¹²)₂,
R² is R¹⁰, CO—R¹⁰, COOR¹⁰ or SO₂R¹⁰,
R⁴ is H or R¹²,
R⁵ is NH₂, H₂N—C(=NH) or H₂N—(C=NH)—NH, where the primary amino groups can also be provided with conventional amino protective groups, or can be mono- di- or trisubstituted by R¹⁰, CO—R¹⁰, COOR¹⁰ or SO₂R¹⁰, or R⁶—NH—,
R⁶ is 1H-imidazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyridin-2-yl, pyrimidin-2-yl or 1,4,5,6-tetrahydropyrimidin-2-yl,
R⁷, R⁸ in each case independently of one another is H or together form a bond,
Z is absent,
R¹⁰ is H, A, Ar or aralkylene having 7–14 C atoms,
R¹¹ is H,
R¹² is alkyl having 1–6 C atoms,
A is H or unsubstituted alkyl having 1–6 C atoms,
Ar is phenyl or naphthyl,
Hal is F, Cl, Br or I,
m is 0,
n is 2, 3 or 4,
or a physiologically acceptable salt or solvate thereof.

23. A compound of formula I

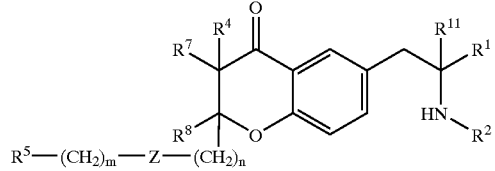

in which
R¹ is CH₂OR¹⁰, COOR¹⁰, CONHR¹⁰ or CON(R¹²)₂,
R² is R¹⁰, CO—R¹⁰, COOR¹⁰ or SO₂R¹⁰,
R⁴ is H or R¹²,
R⁵ is NH₂, H₂N—C(=NH) or H₂N—(C=NH)—NH, where the primary amino groups can also be provided with conventional amino protective groups, or can be mono-, di- or trisubstituted by R¹⁰, CO—R¹⁰, COOR¹⁰ or SO₂R¹⁰, or R⁶—NH—,
R⁶ is 1H-imidazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyridin-2-yl, pyrimidin-2-yl or 1,4,5,6-tetrahydropyrimidin-2-yl,
R⁷, R⁸ in each case independently of one another is H or together form a bond,
Z is absent, O, C(=O) or CH=CH,
R⁹ is H, Hal, OR¹¹, NH₂, NHR¹², N(R¹²)₂, NHAcyl, OAcyl, CN, NO₂, SR¹¹, SOR¹², SO₂R¹² or SO₃H,
R¹⁰ is H, A, Ar or aralkylene having 7–14 C atoms,
R¹¹ is H,
R¹² is alkyl having 1–6 C atoms,
A is H or unsubstituted alkyl having 1–6 C atoms,
Ar is phenyl or naphthyl which is unsubstituted or is mono-, di- or trisubstituted by A and/or R⁹,
Hal is F, Cl, Br or I,
m is 0,
n is 2, 3, or 4,
or a physiologically acceptable salt or solvate thereof.

24. A compound of formula I

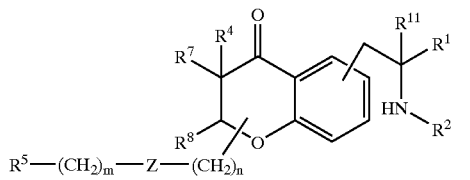

in which
R¹ is CH₂OR¹⁰, COOR¹⁰, CONHR¹⁰ or CON(R¹²)₂,
R² is R¹⁰, CO—R¹⁰, COOR¹⁰ or SO₂R¹⁰,
R⁴ is H or R¹²,
R⁵ is NH₂, H₂N—C(=NH) or H₂N—(C=NH)—NH, where the primary amino groups can also be provided with conventional amino protective groups, or can be mono-, di or trisubstituted by $R^{10}$, CO—$R^{10}$, COOR$^{10}$ or SO$_2$R$^{10}$, or $R^6$ —NH—, $R^6$ is 1H-imidazol-2-yl, 1H-benzimidazol-2-yl, 2H-pyrazol-2-yl, 1H-tetrazol-5-yl, 2-iminoimidazolidin-4-on-5-yl, 1-alkyl-1,5-dihydroimidazol-4-on-2-yl, pyridin-2-yl, pyrimidin-2-yl or 1,4,5,6-tetrahydropyrimidin-2-yl, $R^7$, $R^8$ in each case independently of one another is H or together form a bond, Z is absent, $R^9$ is H, Hal, OR$^{11}$, NH$_2$, NHR$^{12}$, N(R$^{12}$)$_2$, NHAcyl, OAcyl, CN, NO$_2$, SR$^{11}$, SOR$^{12}$, SO$_2$R$^{12}$ or SO$_3$H, $R^{10}$ is H, A, Ar or aralkylene having 7–14 C atoms, $R^{11}$ is H or alkyl having 1–6 C atoms, $R^{12}$ is alkyl having 1–6 C atoms, A is H or unsubstituted alkyl having 1–6 C atoms, Ar is phenyl or naphthyl which is unsubstituted or mono-, di- or trisubstituted by A, and/or $R^9$, Hal is F, Cl, Br or I, m is 0, n is 1, 2, 3 or 4, or a physiologically acceptable salt or solvate thereof.

* * * * *